US009449383B2

(12) United States Patent
Thomson et al.

(10) Patent No.: US 9,449,383 B2
(45) Date of Patent: Sep. 20, 2016

(54) DETERMINATION OF A PHYSICALLY-VARYING ANATOMICAL STRUCTURE

(75) Inventors: Rowena Thomson, Kirchheim (DE); Stephan Mittermeyer, Landshut (DE); Rainer Lachner, Munich (DE)

(73) Assignee: Brainlab AG, Feldkirchen (DE)

( * ) Notice: Subject to any disclaimer, the term of this patent is extended or adjusted under 35 U.S.C. 154(b) by 67 days.

(21) Appl. No.: 14/115,997

(22) PCT Filed: May 17, 2011

(86) PCT No.: PCT/EP2011/057972
§ 371 (c)(1),
(2), (4) Date: Apr. 1, 2014

(87) PCT Pub. No.: WO2012/155964
PCT Pub. Date: Nov. 22, 2012

(65) Prior Publication Data
US 2014/0228676 A1    Aug. 14, 2014

(51) Int. Cl.
*A61B 5/05*   (2006.01)
*G06T 7/00*   (2006.01)
*G06T 7/20*   (2006.01)
*A61B 5/06*   (2006.01)
*G06T 5/50*   (2006.01)

(52) U.S. Cl.
CPC ............ *G06T 7/0012* (2013.01); *A61B 5/061* (2013.01); *G06T 5/50* (2013.01); *G06T 7/0016* (2013.01); *G06T 7/0022* (2013.01); *G06T 7/2006* (2013.01); *G06T 2207/30016* (2013.01); *G06T 2207/30096* (2013.01)

(58) Field of Classification Search
CPC .................... A61B 5/061; G06T 2207/30016; G06T 2207/30096; G06T 5/50; G06T 7/0012; G06T 7/0016; G06T 7/0022; G06T 7/2006
See application file for complete search history.

(56) References Cited

U.S. PATENT DOCUMENTS

| 2002/0012478 A1* | 1/2002 | Thirion | G06T 3/0068 382/294 |
| 2010/0021378 A1* | 1/2010 | Rousso | A61B 5/411 424/1.11 |

OTHER PUBLICATIONS

International Search Report for International Application No. PCT/EP2011/057972 dated Jan. 27, 2012.
Thirion et al., "Deformation Analysis to Detect and Quantify Active Lesions in Three-Dimensional Medical Image Sequences", IEEE Transactions on Medical Imaging, vol. 18, No. 5, May 1999.
Rey et al., "Automatic Detection and Segmentation of Evolving Processes in 3D Medical Images: Application to Multiple Sclerosis", Institut National de Recherche en Infomatique et en Automatique, No. 3559, Nov. 1, 1998, pp. 1-19.

* cited by examiner

*Primary Examiner* — Mark Remaly
(74) *Attorney, Agent, or Firm* — Tucker Ellis LLP

(57) ABSTRACT

The present invention relates to a data processing method for providing variation data which describe a physically-varying anatomical structure, in particular an indiscernible anatomical structure, in particular a non-enhancing tumor, comprising the steps of: providing second image data which describe a second image of a region of an anatomical body, wherein the region includes a second anatomical part which includes the physically-varying anatomical structure; providing first image data which represent a first image of the same region, wherein said same region includes a first anatomical part which does not include the physically-varying anatomical structure or which includes the physically-varying anatomical structure in a different physical state than in the second anatomical part; providing position change data which describe positional changes of corresponding image elements between the first image and the second image, on the basis of the first and second image data; and providing the variation data on the basis of the position change data.

14 Claims, 3 Drawing Sheets

DETERMINATION OF A PHYSICALLY-VARYING ANATOMICAL STRUCTURE

This application is a national phase of International Application No. PCT/EP2011/057972 filed May 17, 2011 and published in the English language.

The present invention relates to the determination of a physically-varying anatomical structure, in particular an indiscernible anatomical structure, in particular a non-enhancing tumour which is within an anatomical body (e.g. human or animal body). The invention relates in particular to the determination of the presence or absence and/or position and/or geometry (i.e. the size and/or shape) of the physically-varying anatomical structure. The term "physically-varying" means in particular that the anatomical structure has undergone a change in its geometry and/or position and/or presence (existence) or absence over time. In particular the anatomical structure expands or shrinks over time. Thus the physically-varying anatomical structure can be an expanded or a shrinked anatomical structure. If in the following an expanded anatomical structure is mentioned, this is meant as an example for the physically-varying anatomical structure. The term "physically varying" means that the physically-varying anatomical structure has varied at least one of its physical properties (position, presence or absence and/or geometry) at least during a time interval in the past but can be invariable (non-changing physical properties) at the time of generating images by an imaging method and/or currently. In other words, there can be time intervals when the physical properties vary and other time intervals when the physical properties are static. If it is mentioned herein that the physically-varying anatomical structure is in a "different physical state", then this means that at least one of the physical properties of the physically-varying anatomical structure has changed. The physically-varying anatomical structure can comprise different elements, for instance growing elements, shrinking elements, necrotic elements, non-proliferative parts. The elements of the physically-varying anatomical structure are in particular cells or cell compounds (e.g. tumour cells). The delineation of the physically-varying anatomical structure can be defined in different ways, for instance in that the concentration of elements of the physically-varying anatomical structure within a healthy anatomical part is below a certain concentration (described e.g. by a percentage of the number of tumour cells related to the total number of cells in a unit volume of the anatomical body) outside the delineation (e.g. a percentage limit of 10%, 5% or 1%). Some of the elements of the physically-varying anatomical structure can be contiguous to and others can be separate from other neighbouring elements of the physically-varying anatomical structure.

In the field of medicine, imaging methods are used to generate image data, for instance two-dimensional or three-dimensional image data, of anatomical structures (such as soft tissues, bones, organs, pathological structures like tumours, edema etc.) of the human body. Analytical devices are in particular used to generate the image data. The imaging methods are in particular used for medical diagnostics, to analyse the anatomical body in order to generate images which are described by the image data. The imaging methods are in particular used to detect pathological physical variations (i.e. change of physical properties) in the human body. However, some of the physical variations in the anatomical structure, in particular the pathological physical variations, in particular physical variations of the pathological anatomical structure (called pathological structure) may not be detectable and in particular may not be visible in the images generated by the imaging methods. A growth of tumour for example represents an example of a physical variation in both the healthy anatomical structure (in which the tumour is embedded) and in the pathological structure (i.e. the tumour). If the tumour had grown, the tumour then represents an physically-varying anatomical structure. If the tumour has responded to treatment, then the tumour represents a shrinked anatomical structure. The physically-varying (in particular expanded or shrinked) anatomical structure may not be detectable by an analytical device; in particular, it may be that only a part of the physically-varying anatomical structure is detectable. Primary/high-grade brain tumours are for example usually visible on MRI scans when using contrast agents to infiltrate the tumour. The MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernible in the image generated by the imaging method. In addition to these tumours, referred to as "enhancing" tumours, there are believed to be approximately 10% of brain tumours which are not discernible on a scan, the tumour itself is in particular not visible to a user looking at the image or images generated by the imaging method. In particular, the physically-varying anatomical structure is not discernible e.g. to a user or an identification algorithm. In other words, just a (suspicious) region of the image (which is filled by the changed anatomical structure, in particular the tumour) do not include image information which allows to determine (identify) the position and/or the presence and/or absence and/or geometry of the changed anatomical structure in the (suspicious) region. In particular the delineation of the changed anatomical structure cannot be determined by a user or an algorithm, at least not determined in an accurate manner if the determination is only based on the image content of the suspicious region.

Analytical devices of for instance x-ray devices, CT devices, MRI devices, ultrasound devices or MRT devices are used to generate analytical images (such as MRI images) of the body. Analytical devices are in particular devices for analysing a patient's body, for instance using waves and/or radiation and/or energy beams, in particular electromagnetic waves and/or radiation, ultrasound waves, particle beams, etc. Analytical devices are in particular devices which generate images (for instance, two-dimensional or three-dimensional images) of the patient's body (in particular of parts of the anatomical body, e.g. of anatomical structures) by analysing the body. Analytical devices are in particular used in medical diagnosis, in particular in radiology.

The following prior art documents relate to non-enhancing tumours:

a) "Automatic Segmentation of Non-enhancing Brain Tumors in Magnetic Resonance Images", Lynn M. Fletcher-Heath, Lawrence O. Hall, Dmitry B. Goldgof and F. Reed Murtagh;
b) US 2007/0133852 A1;
c) US 2007/0280518 A1.
d) "Simulated Brain Tumor Growth Dynamics Using a Three-Dimensional Cellular Automaton", A. R. Kansal, S. Torquato, G. R. Harsh, E. A. Chiocca and T. S. Deisboeck
e) "Temporal Lobe Perfusion Asymmetries in Schizophrenia", James M. Russell, Terrence S. Early, James C. Patterson, Justin L. Martin, Javier Villanueva-Meyer and Molly D. McGee The object of the present invention is to allow the provision of data describing a physically-varying anatomical structure, even if the physically-varying anatomical structure is not discernible.

The above object is solved by the subject-matter of the independent claims. The dependent claims are directed to advantageous embodiments of the invention.

In the following advantages, advantageous features, advantageous embodiments and advantageous aspects of the present invention are disclosed. Different advantageous features can be combined in accordance with the invention.

One feature of the physically-varying anatomical structure is that it is present in a region (referred to as the "varied region" or just in the way of an example as "expanded region") of the anatomical body in which it was not present before. Thus, other anatomical structures (other than the physically-varying anatomical structure) have been displaced by the physically-varying anatomical structure. In particular, at least a part of the displaced anatomical part of the body which was within the expanded region (in which the physically-varying anatomical structure is present) before the displacement is then situated outside the expanded region (in which the physically-varying anatomical structure is present) after the displacement. Herein, a part of the body, i.e. an anatomical part of the anatomical body is shortly called "anatomical part". The present invention preferably uses this displacement to determine data called the physically-varying anatomical structure, in particular to determine variation data which describe the physically-varying anatomical structure, in particular the varied region. In particular, the present invention was image information on the displaced anatomical part.

In the following, the physically-varying anatomical structure is also referred to as the "abnormal anatomical structure", while the anatomical part of the body outside the physically-varying anatomical structure is referred to as the "normal anatomical part". The anatomical part of the body which was present in the expanded region of the physically-varying anatomical structure before the physically-varying anatomical structure emerged and started to expand is also referred to as the "normal anatomical part" and in particular the "displaced normal anatomical part". In accordance with one embodiment of the invention, at least a part of the normal anatomical part, in particular the displaced normal anatomical part, can be detected using imaging methods. In accordance with one aspect of the invention, the displacement of the displaced normal anatomical part is used to infer and in particular determine the physically-varying anatomical structure, in particular in order to determine the physically-varying anatomical structure and in particular the expanded or shrinked region. An anatomical part, in particular a normal anatomical part can comprise one or more anatomical structures or one or more parts of anatomical structures.

The variation data in particular describe the presence or absence and/or position and/or geometry of the physically-varying anatomical structure. The geometry of the physically-varying anatomical structure (and/or the expanded region) is in particular the geometry (i.e. the size and/or shape) of the physically-varying anatomical structure itself, in particular the geometry (i.e. the shape) of the surface of the physically-varying anatomical structure, and/or in particular the geometry (i.e. the size and/or shape) of the delineation (or boundary) of the physically-varying anatomical structure. Instead of or as well as determining the geometry of the physically-varying anatomical structure, the present invention is directed to determining the position of the physically-varying anatomical structure, in particular the position of the surface of the anatomical structure, in particular the position of the delineation (boundary) of the anatomical structure. The present invention is also directed to determining variation data which describe the presence and/or position and/or geometry of the physically-varying anatomical structure (and in particular the expanded region). The variation data in particular allow a determination as to whether a part of the anatomical body forms part of the physically-varying anatomical structure or not. In particular, the variation data describe whether a physically-varying anatomical structure is present or not. The variation data in particular describe the position or positions of at least a part of the physically-varying anatomical structure.

The present invention relates in particular to a data processing method for determining the variation data. This data processing method uses first image data which describe a first image and second image data which describe a second image. Preferably, the first and second image data are designed such that the displacement of the normal anatomical structure due to the expansion of the abnormal anatomical structure can be determined. The variation data are preferably provided, in particular determined, on the basis of the determined displacement.

The method in accordance with the invention is in particular a data processing method. The data processing method is preferably performed using technical means, in particular a computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device. A computer can be a device which is generally thought of as such, such as for example desktop PCs or notebooks or netbooks, etc., but can also be any programmable apparatus, such as for example a mobile phone or an embedded processor. A computer can in particular comprise a system (network) of "sub-computers", wherein each sub-computer represents a computer in its own right. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

Where data are "provided", this means that they are ready for use by the method or program in accordance with the invention. The expression "providing data" encompasses (within the framework of a data processing method) in particular the scenario in which the data are determined by the data processing method or program. The meaning of "providing data" in particular also encompasses the scenario in which the data are received by the data processing method or program (for example, from another program or a data storage), in particular for further processing by the data processing method or program. Thus, "providing data" can also for example mean waiting to receive data and/or receiving the data. The received data can for instance be inputted via the interface. "Providing data" can also mean that the data processing method or program performs steps in order to (actively) acquire the data from a data source, for instance a data storage (such as for example a ROM, RAM, database, hard disc, etc.) or via the interface (for instance, from another computer or a network). The data can achieve the state of being "ready for use" by performing an additional step before the providing step. In accordance with this additional step, the data are generated in order to provide the data. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the providing step), the data can also be provided by performing the additional step of storing the data in a data storage (such as for example a ROM, RAM, CD and/or hard drive), such that they are ready for use within the framework of the method or program in accordance with the invention. The providing step in particular does not involve an invasive step which would represent a substantial physical interference with the body requiring professional medical expertise to be carried out and entailing a substantial health risk even when carried out with the required professional care and expertise. The providing step in particular does not involve a surgical step and in particular does not involve a step of treating a human or animal body using surgery or therapy. This also applies in particular to any steps directed to determining data. Providing first data on the basis of second data means in particular that the second data are used by the method described herein to provide the first data. In order to distinguish the different data used by the method herein, the data are given names (i.e. called) like "XY data" and are defined by the information which they describe.

As mentioned above, one aspect of the present invention is a data processing method for determining the variation data. The data processing method preferably comprises the step of providing the first image data which describe the first image. The first image represents a first anatomical part. The data processing method also preferably comprises the step of providing the second image data which describe the second image. The second image is an image of a second anatomical part. The second anatomical part corresponds to the first anatomical part, wherein "corresponds" means in particular that the second image and the first image show the same region of an anatomical body. In the first image, however, the region does not include the physically-varying anatomical structure or includes the physically-varying anatomical structure in a different physical state than in the second image. The second image in particular shows the same region of an anatomical body as the first image, but the region shown by the second image includes the physically-varying anatomical structure. In other words, the second anatomical part includes the physically-varying anatomical structure which caused (resulted in) the aforementioned displacement of the normal anatomical structure, while the first anatomical part does not include the physically-varying anatomical structure or includes the physically-varying anatomical structure in a different physical state than the second anatomical part. Thus, the first anatomical part does not include a displaced normal anatomical structure or includes a normal anatomical structure which has undergone a smaller displacement (at least on average) than in the second anatomical part.

The second image data provided preferably describe a second image of a region of the anatomical body, and the first image data provided preferably represent a first image of the same region, i.e. if the physically-varying anatomical structure were not present and all anatomical bodies were identical, the anatomical structure in this same region would be identical to the structure present in the region represented by the second image. The first image can in particular be from the same anatomical body as the second image or can be from a different anatomical body to the second image. (The second image can be for instance generated from a database which stores images of the different anatomical body, in particular stores an atlas of the different anatomical body. The different anatomical body can be a real anatomical body of a person or an average (typical) anatomical body as described by an anatomical atlas) The first image can in particular be from the same anatomical body, but at an earlier time than the second image, and represents the same region (referred to as the "anatomical region"). The anatomical region includes the "expanded region". The first image can also be determined, in particular calculated, from a third image of another region of the same anatomical body, wherein the anatomical part in this other region (referred to as the third anatomical part) has symmetry properties with respect to the anatomical structure in the aforementioned anatomical region (referred to above as the "same region") if the anatomical part is normal and healthy, i.e. if the physically-varying anatomical structure is not present in the anatomical region, wherein "symmetry properties" means in particular that if an anatomical region is mirrored at a particular plane (for example, the mid-sagittal plane) or point, this results in a mirrored anatomical region (the mirrored first anatomical part) which is at least similar to said other region (the third anatomical part). Thus, there are a number of ways of providing the first image data. Where it is stated here that the first and second images describe a region or images of a region, this means that the image comprises a representation of this region. Where it is stated here that an image is an image of another anatomical structure, this means that the image comprises a representation of said another anatomical structure, without excluding the possibility that the image also comprises a representation of other anatomical parts, in particular other anatomical structures. In a normal anatomical structure of a normal anatomical body, for example, the anatomical structure at least partly included in the first anatomical part and present in the first region is at least approximately symmetrical to the anatomical structure present in the second region, i.e. there is for example a symmetry property with respect to the sagittal plane, in particular the mid-sagittal plane. Thus, if the first region is for example mirrored at the mid-sagittal plane, this results in a mirrored first region comprising a (mirrored) anatomical structure which is at least similar to the anatomical structure of the second region, i.e. there is for example a symmetry property between the left hemisphere and the right hemisphere of a brain. In accordance with one embodiment, the symmetry property is used to calculate the first image comprising a representation of the first anatomical part, on the basis of a third image comprising a representation of a third anatomical part at the other symmetrical position (for example, the mirrored position) in particular with respect to the sagittal plane (in particular, the mid-sagittal plane). Generating at least part of the first image data from the third image data in particular represents a transformation which involves determining a mirror image of the third anatomical part comprised in the representation of the third image, wherein the plane (with respect to which the third anatomical part of the third image is mirrored) is in particular the sagittal plane. For instance the ventricle structures in a brain exhibit symmetry properties which can be used to generate the first image data.

The image data described here are in particular generated using the above-mentioned imaging methods, such as for instance MRI or CT, in particular in order to generate two-dimensional and preferably three-dimensional images. As mentioned above, the first image data can in particular be generated on the basis of a database comprising images of anatomical parts, in particular anatomical structures, in particular normal anatomical structures, or can be generated on the basis of images of the third anatomical part (which exhibits the aforementioned symmetry properties with respect to the first anatomical part shown by the first image).

Position change data are preferably provided on the basis of the first and second image data. The position change data describe changes in the position of corresponding image elements between the first image and the second image. The corresponding image elements in particular describe the elements of the anatomical part which undergo the aforementioned displacement due to the variation of physical properties of the physically-varying anatomical structure. Thus, the corresponding image elements are in particular outside the physically-varying anatomical structure. Thus, the present invention uses in particular image content which describes part of the anatomical body which is outside the suspicious region.

In accordance with one embodiment of the invention, some corresponding image elements do not change their position due to variation of physical properties of the physically-varying anatomical structure but rather remain at the same position and in particular do not change their geometry. These image elements are referred to as "non-changing corresponding image elements" and can be used to register, in particular to scale and/or align (e.g. by translational and/or rotational transformation) the first and second images with respect to each other, such that there is at least a high degree of similarity in the positions of the non-changing corresponding image elements and in particular a complete overlap of the non-changing corresponding image elements. After this registering, the changes in the position (referred to as the "positional changes") of the corresponding image elements between the first and second images (i.e. from the first image to the second image or from the second image to the first image) can be determined. A vector can for example be determined which connects the position of a first image element to the position of a second image element, wherein the first and second image elements correspond to each other and thus represent corresponding image elements and in particular a "correspondence pair", as will be explained further below. Alternatively or additionally, positional changes can be determined using a transformation from the first image to the second image, in particular by performing dynamic image fusion and in particular image morphing, as will be explained further below. The position change data can be provided automatically or semi-automatically. Providing the position change data semi-automatically in particular involves indicating (in particular, displaying) the first and second images to the user, receiving data which describe the positions of corresponding image elements and subsequently determining the position change data on the basis of the corresponding image elements received. As mentioned above, the position change data can also be provided automatically, by determining the position change data on the basis of the first and second image data by transforming and/or scaling and/or aligning the images. Automatically providing position change data in particular involves analysing the first and second image data in order to determine corresponding image elements. This analysis in particular involves determining similarities, in particular similarities between the images and/or similarities in the position and/or geometry of corresponding image elements.

Variation data are preferably provided on the basis of the position change data. This means in particular that the position change data are used by the data processing method to provide the variation data. The variation data describe the physically-varying anatomical structure, in particular the presence or absence and/or position and/or geometry of the physically-varying anatomical structure, in particular the position and/or geometry of the delineation (boundary) of the physically-varying anatomical structure, in particular the position and/or surface of the physically-varying anatomical structure.

The variation data can be provided semi-automatically, for instance by indicating the positional changes described by the position change data (to a user) for instance by outputting an indication using indication signals (audio, video, tactile), in particular an image via a user interface, in particular graphical user interface GUI (which indication, in particular image represent the positional changes described by the position change data) and then receiving the variation data by means of a user input. Thus the variation data are provided on the basis of the position change data. In particular, the semi-automatic provision represents an example of using the position change data for providing the variation data. The magnitude and/or direction of positional changes can in particular be indicated to the user in accordance with the positions of "sub-regions" which are parts of the region shown by the first and second image. A sub-region can be an extended part of a region or a point. A plurality of displayed vectors (originating at the positions of different sub-regions) can indicate the magnitude and/or direction of the positional changes of the sub-regions to a user. This enables a user to infer the position and/or geometry, in particular the surface, in particular the delineation, of the physically-varying anatomical structure, since the positional changes of the sub-regions due to the expansion are for example indicated to a user. The user can input the result of this inference into the data processing method. In other words, the data processing method receives the variation data from the user after indicating the position change data to the user. In accordance with another embodiment, the variation data are provided automatically, in particular by being determined (automatically) from the position change data, as will be explained in more detail further below. Thus, the variation data are provided (i.e. automatically determined) on the basis of the position change data. In particular, the automatic determination represents an example of using the position change data for providing the variation data. The variation data are in particular determined by analysing the positional changes, particularly if the positional changes indicate a local expansion or compression in volume.

In accordance with one embodiment of the data processing method, the step of providing the position change data involves (automatically) determining a transformation in order to transform the first image and/or the second image. The transformation is preferably described by data called transformation data. If the transformation is applied to the first image, then the transformation results in a transformed image (referred to as the transformed first image). The transformation is preferably such that the transformed first image is at least similar to the second image, wherein "at least similar" means in particular that the transformed first image is more similar to the second image than the (untransformed) first image.

Within the context of this application, "at least similar" means in particular that the degree of similarity is above a certain predefined threshold. The "measure of image similarity" quantifies the degree of similarity between two images (in the given example, between the second image and the transformed first image). Examples of measures of image similarity include for instance the sum of squared intensity differences between the images, cross-correlation, mutual information and the ratio of image uniformity, and normalised mutual information. The threshold can be defined such that the degree of similarity is at least 70%, 80%, 90%, 95% or 99%. In accordance with one embodiment, different candidates for the transformation are provided and applied to the first image. The measure of image similarity is then calculated for each candidate. The candidate transformation selected is the one which results in the transformed first image exhibiting the greatest similarity (i.e. the highest degree of similarity or greatest measure of image similarity) to the second image. In accordance with another embodiment, the second image is transformed into a transformed second image which is preferably at least similar to the first image. In this case, too, "at least similar" has the corresponding meaning described above and the transformation can in particular be determined by providing a plurality of candidate transformations and selecting the one which results in the transformed second image exhibiting the greatest similarity to the first image. The transformation preferably describes the positional changes between the first image and the transformed first image and/or between the second image and the transformed second image. These positional changes are deemed to be the positional changes described by the position change data and are in particular deemed to be the positional changes of corresponding image elements between the first and second images. In accordance with this embodiment, the position change data describe positional changes experienced by image elements when the determined transformation is applied. These positional changes are deemed to represent the positional changes of corresponding image elements between the first and second images. The transformation can in particular be described using a vector field. The bases of the vectors of the vector field preferably describe the positions of image elements in the untransformed image, and the tips of the vectors describe the positions of the corresponding image elements (in particular, the same image elements) in the transformed image.

The transformation is preferably determined on the basis of an image morphing algorithm. The image morphing algorithm is preferably applied to the first image or the second image in order to transform one of the first and second images into the other of the first and second images. In this application, the term "image morphing" is also used as an alternative to the term "image fusion", but with the same meaning.

Image morphing transformations are in particular designed to enable a seamless transition from one image to another image. The transformation is in particular designed such that one of the first and second images is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in optimum similarity. As mentioned above, the degree of similarity is preferably measured by way of a measure of similarity (also referred to in the following as a "similarity measure"). The parameters of the optimisation algorithm are in particular vectors of a deformation field F. These vectors are determined by the optimisation algorithm which results in optimum similarity. Thus, optimum similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (further) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting, in particular that the transformed (deformed) image does not comprise faults and/or raptures. The constraints include in particular the constraint that in case a regular grid is transformed. Simultaneously with the image and in a corresponding manner, then the grid is not allowed to interfold at any of its locations. The optimising problem is in particular solved iteratively, in particular by means of an optimisation algorithm which is in particular a first-order optimisation algorithm, in particular a gradient descent algorithm. Other examples for optimisation algorithms are optimisation algorithms which do not use derivations like the Downhill Simplex algorithm or algorithms which use higher order derivatives like Newton-like algorithms. Preferably, the optimisation algorithm perform a local optimisation. In case of a plurality of local optima, global algorithms like Simulated Annealing or Genetic Algorithm can be used. In case of non-linear optimisation problems for instance the Simplex method can be used.

In the steps of the optimisation algorithms, the voxels are in particular shifted by a magnitude in a direction such that the degree of similarity is increased. This magnitude is preferably less than a predefined limit, for instance less than $1/10$ or $1/100$ or $1/1000$ of the diameter of the image, and in particular about equal to or less than the distance between neighbouring voxels. Due in particular to a high number of (iteration) steps, large deformations can be implemented.

As mentioned above, the position change data are preferably determined by determining a similarity measure on the basis of the first and second image data. In particular, the similarity between the first and second image or between corresponding elements of the first and second images is determined. In particular, the similarity between one of a transformed first image and a transformed second image and the other of the first image and second image is determined. In particular, the similarity between image elements (for example, voxels) of the transformed first or second image and image elements of the other of the first image and second image are determined.

In accordance with one embodiment, correspondence data are provided on the basis of the first and second image data. The step of providing correspondence data can be a step of receiving the correspondence data, for example via a user interface, wherein a user for example inputs the correspondence data into the data processing method. The step of providing the correspondence data can also include the step of indicating the first and second image data to the user. Providing the first and second image data thus comprises the steps of indicating the first and second image (on the basis of the first and second image data) and receiving the correspondence data. A user can for instance mark correspondence pairs on a screen. The marked pairs are received by the data processing method. The user can also for example mark typical landmarks of a brain which correspond to each other and which are shifted due to the expansion of a tumour. The landmark is then marked in the first image, and the corresponding (shifted) landmark is marked in the second image. The two marked landmarks then represent an example of a correspondence pair, which is inputted into the data processing method which is being run on a computer.

In accordance with an alternative embodiment, the step of providing the correspondence pairs is performed automatically, i.e. an algorithm analyses the first and second images for image elements which are at least similar and for example represent landmarks of the anatomical structure which are shown by the first and second images. In this way, a landmark and a shifted landmark can be automatically identified in the first and second images. The correspondence pairs are thus automatically identified.

The correspondence data comprise a description of correspondence pairs. The correspondence pairs are pairs of corresponding image elements of the first and second images. These pairs of corresponding image elements are also referred to as "pairs of elements" or short. A correspondence pair, in particular each correspondence pair, includes and in particular consists of a first element and a second element. The first element is in particular an image element of the first image, and the second element is in particular an image element of the second image. In particular, the first and second image elements correspond to each other. This means in particular that they are at least similar to each other, wherein "at least similar" has the meaning mentioned above, i.e. that the first and second images are for example more similar to each other than to other image elements and/or that the first and second image elements exhibit a degree of similarity which is greater than a certain threshold and/or that neighbouring elements are also at least similar to each other, as will be explained further below. The correspondence data in particular describe the positions of the first and second elements in the first and second images, respectively. As mentioned above, a similarity measure is determined in accordance with one embodiment on the basis of the first and second image data. The position change data are preferably provided on the basis of the determined similarity measure. Determining the similarity measure on the basis of the first and second image data can also be part of the embodiment described below. An image element can for instance comprise one or more voxels.

In accordance with one embodiment of the invention, the data processing method comprises the step of providing correspondence data on the basis of the first and second image data. The correspondence data comprise a description of correspondence pairs (already mentioned above) which are pairs of elements of the first and second images. A first element (also referred to as the "first image element") of the correspondence pair is an image element of the first image. The second element (also referred to as the "second image element") of the pair is an image element of the second image. The first and second elements are examples of corresponding image elements. Preferably, the first and second image element of a correspondence pair are at least similar to each other.

The positional change data are provided, in particular determined, on the basis of the correspondence data. The positional change data are determined on the basis of the positions of the first and second elements of a correspondence pair. The position change data are in particular determined such that they represent a positional change which corresponds to a change in position from the position of one of the first and second elements of a correspondence pair to the position of the other of the first and second elements of the same correspondence pair. The change from a first position of the first element to a second position of the second element and/or from a second position of the second element to a first position of the first element is preferably determined for each of the correspondence pairs. The positional change is for instance represented by a vector, and the plurality of positional changes can be represented by a vector field.

In accordance with one embodiment, position identity data are provided which describe the pairs which are assumed to represent correspondence pairs which have not undergone a change in position. Some body parts which are for example distant from the physically-varying anatomical structure will not have been displaced, in particular deformed, by the physically-varying anatomical structure. These body parts are preferably described by image elements (the aforementioned non-changing corresponding image elements), the position of which is preferably described by the above-mentioned position identity data. These position identity data can be used to register, in particular to scale and/or align the first and second images. The position change data are preferably determined on the basis of the positions of the elements of correspondence pairs after scaling has been performed if necessary. It is also possible for the first and second images represented by the first and second image data to already be registered before they are processed by the data processing method in accordance with the invention. In order to determine the position change data, the first and second images are for example registered with respect to each other, such that the identical image elements (the position of which is described by the position identity data) overlap completely. The difference in position between a first and second element (described for example by a vector) is then preferably determined and represents a positional change of a pair of corresponding image elements. If the image elements are identical, then the positional change equals zero. However, a plurality of corresponding image elements, in particular correspondence pairs, preferably represent a positional change which is greater than zero. The positional change can in particular be described by a vector from one of the first and second elements to the other of the first and second elements of a correspondence pair.

As mentioned above, the correspondence data can be provided in a variety of ways. They can for example be provided semi-automatically by outputting indication data which represent the first and second images, in particular to a display, such that the first and second images are shown on the display. A user can then for example indicate correspondence pairs on the display, for example by marking the corresponding elements on the displayed first and second images, wherein the marked elements are then received as correspondence data. The correspondence data in particular describe the position of the first element in the first image and the position of the second element in the second image of a correspondence pair designated (for example, marked) by a user.

In accordance with another embodiment which can be combined with the aforementioned embodiment, a plurality of image element datasets are provided. The image element data can be provided by indicating the first and second images, as mentioned above, when receiving a plurality of image elements which have for instance been designated by the user. The data processing method then determines whether the designated image elements correspond to each other, as will be explained further below. In accordance with another embodiment, a plurality of image elements are automatically determined, wherein elements of the image are for example selected which exhibit at least one of the following features: a contrast above a certain threshold value; an image energy level above a certain threshold value; a difference between the maximum grey level and minimum grey level in the image element which is above a certain threshold value, etc. In accordance with another embodiment, the first and second images are tessellated into a plurality of image elements. Preferably, the image elements provided are compared with each other in order to determine a correspondence pair, wherein two of the plurality of image elements provided are preferably determined such that they represent the correspondence pair if at least one of the following conditions is fulfilled:

a) in accordance with a first condition, the two image elements (which are for instance compared with each other) are described by received correspondence data which specify that the two image elements represent a correspondence pair. A plurality of image elements are for example shown to a user on a display. A grid is for example superimposed over the first and second displayed images, on the basis of the first and second image data. The grid defines a plurality of image elements of the first and second images. The user can then designate two of the image elements which are believed to correspond to each other. The correspondence data are generated on the basis of this designation. The data processing method can then check whether the received correspondence data, i.e. the received pair of image elements, fulfil a condition of sufficient similarity (for instance to the effect that the similarity measure has to be above a certain threshold). The data processing method for example accepts the received correspondence data as "provided correspondence data" only if the condition is fulfilled.

b) In accordance with another embodiment, two image elements are in particular automatically determined such that they represent a correspondence pair if at least one of the following conditions applies:
  i) the image content of one of the two image elements (also referred to in the following as the "first image element") is at least similar to the image content of the other of the two image elements (also referred to in the following as the "second image element"). The term "at least similar" has already been described above. The image content is in particular described by the one or more voxels (which the image elements include) if the image is a three-dimensional image or by the one or more pixels (which the image element includes) if the image is a two-dimensional image. Similarity measures are in particular used to determine the similarity of the image content. In particular, the image content represents the image represented by the image element. In accordance with one embodiment, the geometry of the first image element is in particular allowed to be different from the geometry of the second image element. The change in the geometry of an element of a body part due to the deformation can thus be considered; and/or
  ii) in accordance with another condition, the similarity of neighbouring image elements which neighbour the first image element is considered. In particular, the similarity between neighbours of the first image element and neighbours of the second image element is determined; in particular, it is determined whether they are at least similar. If they are at least similar, then the first and second image elements are in particular considered to represent a correspondence pair. The data processing method in particular uses correspondence pairs which have already been determined in order to determine whether the neighbourhood of two image elements fulfils the similarity requirements. To this end, a first neighbouring image element for example neighbours a first image element and is also an element of a correspondence pair which has already been determined. It is also assumed that the second element of this correspondence pair likewise neighbours the second image element. In accordance with one embodiment, a similarity condition with respect to the neighbourhood is fulfilled if the relative position between the first neighbouring image element and the first image element is at least similar to the relative position between the second neighbouring image element and the second image element. An at least similar relative position can be defined as being fulfilled if for instance the distance does not deviate by more than one percent, five percent or ten percent and/or if the direction represented by a vector connecting the first neighbouring image element to the first image element and another vector connecting the second neighbouring image element to the second image element is within a predefined range. Preferably, the similarity condition for the neighbourhood is deemed to be fulfilled if the relative positions are similar for a plurality of first and second neighbouring image elements, wherein the first neighbouring image elements neighbour the first image element and the second neighbouring image elements neighbour the second image element. The similarity condition is in particular deemed to be fulfilled if the plurality of first and second neighbouring image elements which fulfil the similarity condition exceed a certain number and/or if the similarity condition is fulfilled for the majority of first and second neighbouring image elements and/or if the similarity condition is fulfilled for the relative positions of more than a certain percentage of the first and second neighbouring image elements (in particular, more than 60%, 70%, 80% or 90%).

c) In accordance with another embodiment, two image elements are determined to be corresponding image elements of a correspondence pair if one of the first and second image elements is transformed into a third image element by a transformation and the third image element has the same position as the other of the two image elements. The transformation is a transformation which transforms one of the first and second images into the other of the first and second images. The transformation in particular uses an image forming algorithm. The transformation is thus used to determine whether an image element of the first image corresponds to an image element of the second image. The transformation is in particular a transformation such as already been described above, i.e. a transformation which transforms one of the first and second images into a transformed image which is at least similar to the other of the first and second images. The transformed image comprises the third image element.

The data processing method preferably allows a delineation of the physically-varying anatomical structure to be determined. To this end, the position change data preferably comprise data which describe the positions at which the positional changes occur. These positions are referred to here as "change positions". The positional changes are for example described by vectors. Each vector is preferably assigned a position which describes the position of the vector. In accordance with one embodiment, a plurality of vectors are provided, in particular a vector field. This field in particular describes the deformation of the first image into the second image and is therefore also referred to as the deformation field (as already mentioned above). The deformation field is a function of the positions (i.e. the change positions). The deformation field is referred to here in an abbreviated form as F(r), wherein the letter "r" represents the change position (in two or three dimensions) and can for instance be described by two (x, y) or three co-ordinates (x, y, z). The function F is in particular a vector which in particular describes the positional changes of pixels or voxels in accordance with the change positions.

In accordance with this embodiment, compression-variation data are preferably determined on the basis of the positional changes at the change positions, in particular on the basis of F(r). The compression-variation data preferably describe where a transition between a compression and an expansion occurs. In the case of three-dimensional images, the multiplicity (manifold) of positions at which the transition between the compression and the expansion occurs is in particular a surface, in particular a closed surface (a closed multiplicity in two dimensions) which includes at least some and preferably all of the physically-varying anatomical structure and which in particular surrounds the physically-varying anatomical structure. This surface is also referred to here as the "variation surface". The delineation of the physically-varying anatomical structure is in particular determined on the basis of the variation surface; in particular, the variation surface is deemed to correspond to the delineation.

The variation surface can be determined in different ways. Additional embodiments featuring alternative methods for determining the variation surface will be described below.

In accordance with one embodiment, the delineation—in particular, the position and/or geometry of the delineation—is determined on the basis of the determined variation surface. Preferably, a database is accessed which stores the relationship between the geometry of the variation surface and the geometry of the delineation of the physically-varying anatomical structure. The database in particular comprises relationship data which describe this relationship for different types of physically-varying anatomical structures (in particular, tumours) and/or different types of anatomical body parts in which the physically-varying anatomical structure is present. The relationship data can for example describe that the physically-varying anatomical structure is greater or smaller than the variation surface by a predefined factor (multiplier). This factor is in particular determined such that there is a high probability that the physically-varying anatomical structure is within the delineation. The factor is an example of the relationship between the aforementioned geometries of the variation surface and physically-varying anatomical structure. The factor can depend on the aforementioned types, as described by the relationship data. This can reduce the risk of parts of the anatomical structure, in particular parts of the tumour, remaining in the body part after surgery.

In accordance with another embodiment, the variation surface is determined on the basis of the position at which the positional change is at a maximum. In this respect, it is referred to A. R. Kansal et. al. J. theor. Biol. (2000), 203, 367-382 "Simulated Brain Tumor Growth Dynamics Using a Three-dimensional cellular Automation".

The variation data preferably comprise a description of the position and/or geometry of the variation surface and/or of the delineation.

In accordance with one embodiment, a region of the second image is determined to be a region in which expansion has occurred if voxels within the region are described (on the basis of the position change data) as having changed their position towards the outer surface of this region. A region is also in particular described as being a region in which compression has occurred if the position change data indicate that the voxels inside the region have been displaced towards the centre of the region. In accordance with this embodiment, the variation surface is determined to be between regions in which an expansion has occurred and regions in which a compression has occurred.

In accordance with another embodiment, the positional changes are represented by a vector field, and the variation data are determined by calculating a determinant of a Jacobian matrix of the vector field. This vector field is in particular the aforementioned deformation field F(r). The Jacobian determinant is preferably calculated for the plurality of positions r. The Jacobian determinant describes the change in volume at the position r and is equal to one if there is no change in volume, but greater than one if there is an expansion at the position r and less than one if there is a compression at the position r. In accordance with one embodiment, the Jacobian determinant is equal to one at a plurality of positions, and these positions span the variation surface or represent the variation surface (if the plurality is a manifold). The transition between the compression and the expansion is in particular described as occurring at positions which are between positions at which the Jacobian determinant is smaller than one and positions at which the Jacobian determinant is greater than one. An expansion in volume is in particular assumed to represent the growth of a tumour, and a compression in volume is in particular assumed to represent a compression of the normal anatomical structure. An expansion of the volume which encompasses (but does not include) the physically-varying anatomical structure can in particular present a shrinkage of the tumour and a compression of the volume (in which the physically-varying anatomical structure is present) can also represent a shrinkage of the tumour.

As mentioned above, a variation surface which is determined on the basis of the Jacobian determinant can be used as a basis for determining the delineation of the physically-varying anatomical structure, for instance on the basis of a database as described above.

In accordance with another embodiment, the variation data are provided semi-automatically. In accordance with this embodiment, the data processing method outputs change indicating data and receives the variation data. The change indicating data indicate the positional changes, in particular the magnitude and/or direction of the positional changes. The change indicating data are for example displayed on a display and for example describe a plurality of vectors which represent the positional changes. Alternatively or additionally, the change indication data indicate the change in volume and in particular describe the degree of expansion and/or compression. The degree of positional change and/or the degree of compression and/or expansion can for instance be colour-coded, and the corresponding parts in at least one of the first and second images can be coloured accordingly, wherein the colour in particular represents the degree of change. A user viewing the display can thus see which parts of the image have been compressed and which parts have expanded due to the growth of the physically-varying anatomical structure. The data processing method preferably comprises an inputting step in order to receive the variation data which are inputted by a user. The user can for instance mark the parts on an image which are believed to represent the delineation of the physically-varying anatomical structure, wherein the displayed indication data assist the user during this marking process.

The present invention is also directed to a navigation system for computer-assisted surgery. This navigation system preferably comprises the aforementioned computer for processing the data provided in accordance with the data processing method as described in any one of the preceding embodiments. The navigation system preferably comprises a detection device for detecting the position of the detection points which represent the main points and auxiliary points, in order to generate detection signals and to supply the detection signals generated to the computer such that the computer can determine the absolute main point data and absolute auxiliary point data on the basis of the detection signals received. In this way, the absolute point data can be provided to the computer. The navigation system also preferably comprises a user interface for receiving the calculation results from the computer (for example the position of the main plane, the position of the auxiliary plane and/or the position of the standard plane). The user interface provides the received data to the user as information. Examples of a user interface are a monitor or a loudspeaker. The user interface can use any kind of indication signal (for example a visual signal, an audio signal and/or a vibration signal).

The present invention is also directed to a method for navigating an instrument, in particular using the above-mentioned navigation system. The method in particular comprises the steps, in particular all of the steps, of one of the embodiments described above, in particular in order to determine the variation data. In addition to the steps of the above-mentioned embodiments of a data processing method, the method for navigating an instrument also preferably comprises the step of providing instrument position data which describe the position of an instrument. A marker device is for example attached to an instrument, and the markers of the marker device are detected by the detection device of the navigation system. The detection device in particular comprises one or more cameras.

It is the function of a marker to be detected by a marker detection device (for example, a camera or an ultrasound receiver), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or a pointer or one or more (individual) markers in a predetermined spatial relationship. A marker device comprises one, two, three or more markers in a predetermined spatial relationship. This predetermined spatial relationship is in particular known to a navigation system and for example stored in a computer of the navigation system.

The method also preferably comprises the step of providing body part position data. Body part position data describe the position of the second anatomical part. The body part position data can for instance be generated using analytical devices which can in particular be used for imaging methods. Analytical devices such as x-ray devices, CT devices, MRI devices or MRT devices can be used to generate analytical images (such as x-ray images or MRT images) of the body. Analytical devices are in particular devices for analysing a patient's body, for instance using waves and/or radiation and/or energy beams, in particular electromagnetic waves and/or radiation, ultrasound waves, particles beams, etc. Analytical devices are in particular devices which generate images (for instance, two-dimensional or three-dimensional images) of the patient's body (in particular, internal structures and/or anatomical parts) by analysing the body. Analytical devices are in particular used in medical diagnosis, in particular in radiology.

In accordance with one embodiment, a marker device is attached to the body in a fixed position relative to the second anatomical part. The position of the marker device relative to the second anatomical part is known on the basis of the images, in particular three-dimensional images, of the second anatomical part which preferably also include an image of the marker device. The relative position between the instrument and the second anatomical part can be determined, in particular calculated, on the basis of detecting this marker device which is attached to the body and on the basis of the detected position of the instrument.

In accordance with the method for navigating an instrument, the position of the instrument relative to the physically-varying anatomical structure is preferably determined on the basis of the variation data, instrument position data and body part position data. In accordance with a preferred embodiment of the present invention, the variation data describe the position of the physically-varying anatomical structure relative to the second anatomical part, in particular the position of the variation surface, in particular the position of the delineation (in particular surface) of the physically-varying anatomical structure relative to the second anatomical part, i.e. in particular in a reference system in which the second anatomical part lies. The variation data in particular describe the position (and geometry) of the expansion region within the second anatomical part. In particular, the relative position between the second anatomical part and the instrument is calculated on the basis of the instrument position data and the body part position data. The relative position between the instrument and the physically-varying anatomical structure, in particular the variation surface, in particular the delineation of the physically-varying anatomical structure, is then calculated on the basis of the variation data which describe the relative position between the physically-varying anatomical structure and the second anatomical part, wherein "geometry" means size and/or shape.

The present invention is also directed to a program which, when running on a computer or when loaded onto a computer, causes the computer to perform the steps of at least one of the above-mentioned embodiments of the data processing method. The present invention is also directed to a program storage medium, in particular a non-transitory program storage medium on which the program is stored. The present invention is also directed to a computer on which the program is running or into the memory of which the program is loaded, in particular in a non-transitory form. The present invention is also directed to a signal wave, in particular a digital signal wave, carrying information which represents the program. The program in particular comprises code means which are adapted to perform the steps of at least one of the embodiments of the data processing method described herein and in particular all of the steps of the respective embodiments.

As mentioned above, the present invention is in particular directed to a navigation system which is in particular used in computer-assisted surgery. The navigation system preferably comprises the aforementioned computer for determining the variation data and a detection device for detecting the position of the instrument and the position of the second anatomical part. The detection device is preferably designed to transmit the detection signals to the computer. The computer is preferably designed to receive the detection signals and in particular to transform the detection signals into the detection data. The detection data in particular comprise the above-mentioned instrument position data. The computer is also preferably designed to receive body part position data which can be generated by the above-mentioned analytical devices which generate an image of the second anatomical part by means of the above-mentioned imaging method. The body part position data are calculated on the basis of the known spatial relationship between the reference system of the navigation system and the region displayed by the images generated by the analytical device. Additionally or alternatively, the detection device can be used to detect a marker device which is attached to the anatomical body, in order to generate the body part position data. The relative positions between the marker device which is attached to the anatomical body and the second anatomical part are preferably determined by analysing the images generated by the analytical devices. The analytical devices preferably detect both the structure of the second anatomical part and the marker device which is attached to the anatomical body. The relative position between the marker device which is attached to the body and the second anatomical part is determined on the basis of these images. The detection device also preferably detects the position of the marker device which is attached to the anatomical body. The analytical device preferably transmits a signal, which represents the image generated from the anatomical body and the marker device, to the computer. The detection device also preferably transmits signals, which represent the position of the marker device which is attached to the anatomical body, to the computer. The computer preferably determines the body part position data, which describe the position of the second anatomical body in a reference system of the navigation system, in particular relative to the position of the instrument, on the basis of these two signals.

Within the framework of the invention, computer program elements can be embodied by hardware and/or software (this also includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of this invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The analytical device is in particular designed such that it cannot detect the delineation of the physically-varying anatomical structure and/or the physically-varying anatomical structure itself and/or a portion of the physically-varying anatomical structure, but can in particular detect at least some (in particular, most) of the remainder of the second anatomical part which does not form part of the physically-varying anatomical structure. The analytical device is in particular designed to detect the delineation of the remainder, in particular the delineation which is adjacent to the physically-varying anatomical structure and/or encloses the physically-varying anatomical structure. The body part position data in particular describe the position and/or geometry (i.e. the size and/or shape) of the second anatomical part, in particular within the reference system of the navigation system.

The navigation system also preferably comprises an indication device for visually and/or acoustically and/or tactilely indicating the determined relative position (between the instrument and the physically-varying anatomical structure). The indication device receives said data from the computer. The indication device can be a display, loudspeaker, vibration element, etc. The indication device is designed to generate indication signals (for instance, images or sounds) on the basis of the received data, in order to indicate the relative position between the instrument and the physically-varying anatomical structure. The computer in particular comprises an interface which converts data into signals, such as for instance electrical signals or optical signals. The interface in particular converts indication data into indication signals for indicating: the position change data; the magnitude and/or direction of positional changes of corresponding elements, in particular correspondence pairs; the expanded structure, in particular the position and/or geometry of the expanded structure; a delineation of the expanded structure, the variation surface and/or the relative position between the instrument and the expanded structure. The signals are in particular technical signals.

The following detailed description of the invention discloses additional embodiments, in particular features, of the invention. Different features of different embodiments can be combined.

The following detailed description refers just as an example to the case where the variation of physical property is an expansion. Thus, the physically-varying anatomical structure is an "expanded structure".

Figure 1:
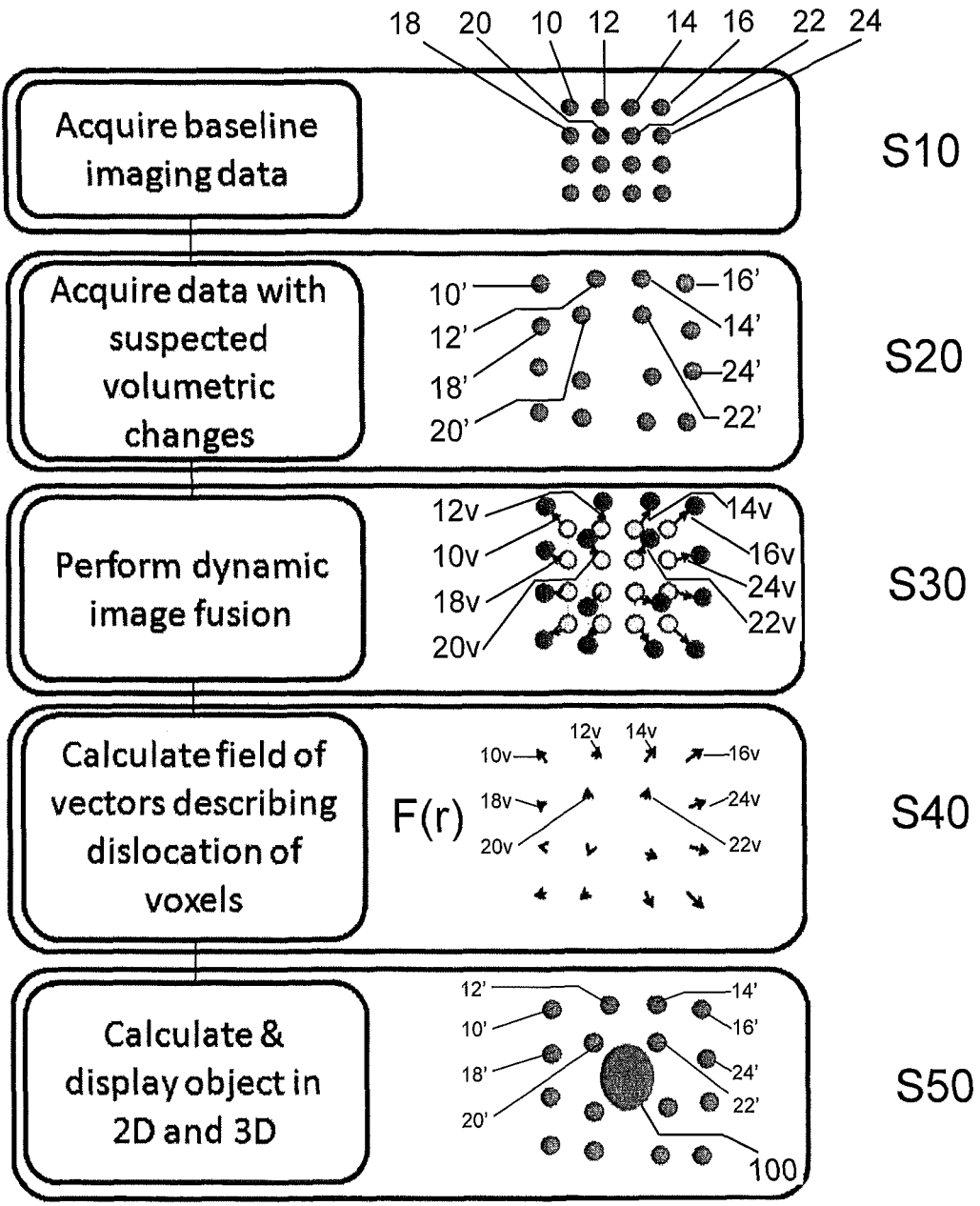
FIG. 1 shows the steps of a method in accordance with the invention.

FIG. 1 shows five steps which form part of a method in accordance with an embodiment of the invention and bear the reference signs S10, S20, S30, S40 and S50, respectively. A small illustration appears immediately to the left of each of the reference signs "S10" to "S50", and these are referred to as "sub-figures". These sub-figures are thus referred to as sub-figures "S10" to "S50", respectively.

Step S10 relates to acquiring baseline imaging data. These baseline imaging data represent the aforementioned first image data. The baseline image data show an anatomical structure which does not include a physically-varying anatomical structure. As mentioned above, the baseline image data (first image data) can be acquired by means of analytical devices. Thus, the result of step S10 is that the first image data are provided. Sub-figure S10, between the method step description "acquire baseline image data" and the reference sign "S10", represents a grid of image elements of the first image, some of which bear reference signs (10, 12, 14, 16, 18, 20, 22 and 24). These image elements are in particular distinguishable image elements which in particular exhibit an identifiable structure. The image elements represent elements of the first anatomical part.

Step S20 relates to providing the second image data. The second image data are provided by acquiring data with suspected volumetric changes. The image elements 10' to 24' (in sub-figure S20) represent elements of the second anatomical part which includes the indiscernible (invisible) physically-varying anatomical structure. The physically-varying anatomical structure causes the image elements 10 to 24 to be displaced to the positions of the image elements 10' to 24'. Thus, the image elements 10 to 24 of S10 are shown as the displaced image elements 10' to 24' in sub-figure S20 between the method step description "acquire data with suspected volumetric changes" and the reference sign "S20" in FIG. 1. The image elements of sub-figure S20 (which correspond to the image elements of sub-figure S10) are accordingly marked with the same reference number as the image elements of sub-figure S10, but with a prime, such that the image element 10 in sub-figure S10 corresponds to the image element 10' in sub-figure S20, the image element 12 in sub-figure S10 corresponds to the image element 12' in sub-figure S20, etc. By comparing the sub-figure shown in S10 with the sub-figure shown in S20, it can be seen that the image elements 10' to 24' in sub-figure S20 have been displaced as compared to the image elements 10 to 24 in sub-figure S10, such that there is a void in the middle of the image elements of sub-figure S20 which may be due to an expanded structure which is not discernible, i.e. the expanded structure is in particular not shown in sub-figure S20 which is in particular generated using an analytical device. Sub-figure S10 corresponds to the first image described by the first image data, and sub-figure S20 corresponds to the second image described by the second image data.

Both sub-figure S10 (which is a simplified example of a first image) and sub-figure S20 (which is a simplified example of a second image) are preferably used in step S30. Steps S30 and S40 are preferably used to provide the position change data.

In step S30, a transformation is preferably determined which, if applied to the first image (sub-figure S10), transforms the first image into the second image (sub-figure S20). The transformation results in particular from dynamic image fusion, in particular from an image morphing process which morphs the first image into the second image. The transformation determined in step S30 in particular represents the positional changes (10v to 24v shown in sub-figure S30) of the corresponding image elements. The transformation can be represented by a vector field F(r) (see sub-figure S40), wherein the vectors 10v, 12v, 14v, 16v, 18v, 20v, 22v and 24v of the vector field in particular represent the positional changes of the corresponding image elements from the position of the image elements 10, 12, 14, 16, 18, 20, 22 and 24 to the position of the image elements 10', 12', 14', 16', 18', 20', 22' and 24'. The vectors in particular describe the dislocation of voxels of the first image which results in an image which is at least similar to the second image and preferably identical to the second image.

Step S50 relates to providing the variation data. In step S50, the variation data are determined on the basis of the vector field determined in step S40. The variation data in particular describe the position and geometry of the physically-varying anatomical structure 100 which is shown in sub-figure S50 (between the method step description "calculate and display object in 2D and 3D" and the reference sign "S50"). As mentioned above, the surface of the expanded structure (the "variation surface") can in particular be calculated on the basis of a determinant of the Jacobian matrix of the vector field determined in step S40. The surface of the expanded structure 100 is in particular determined by setting the Jacobian determinant to 1. The vectors of the vector field are a function of the position within the second image. The variation surface is in particular defined by the positions at which the determinant of the Jacobian matrix equals 1.

Figure 2:
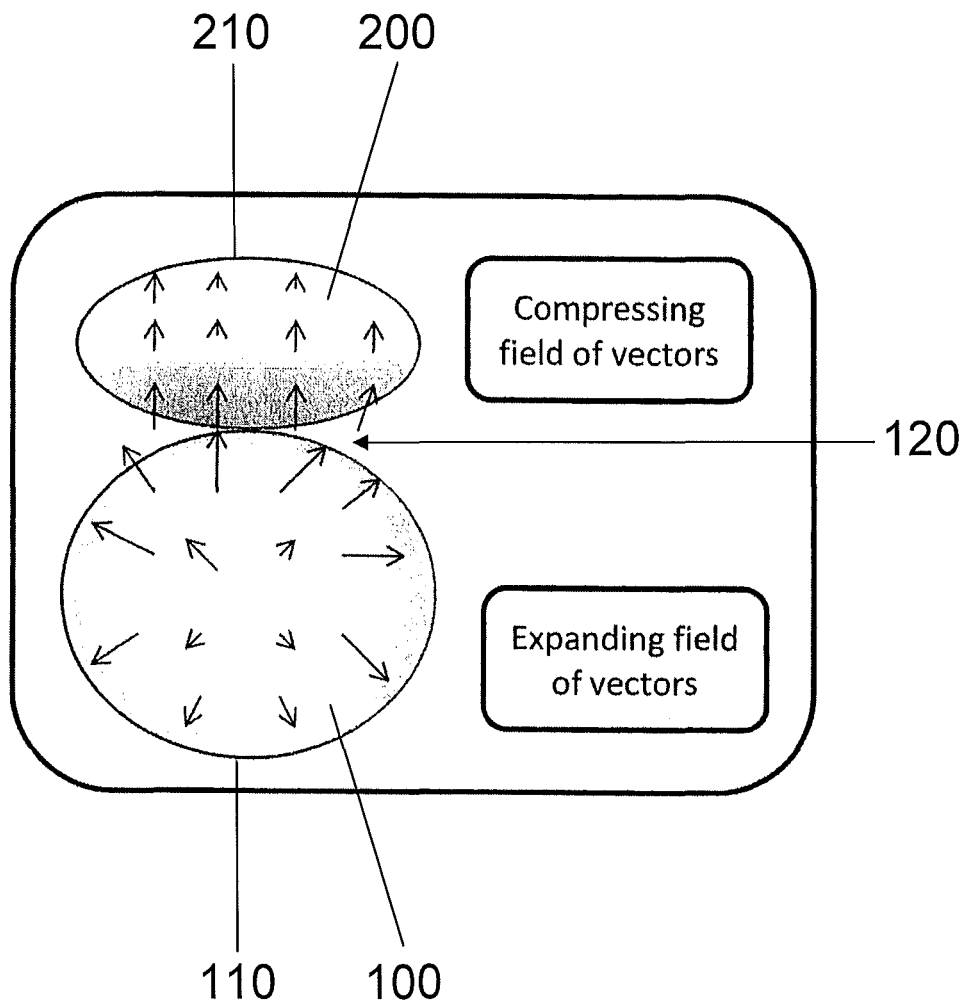
FIG. 2 shows the compression and expansion of a vector field.

FIG. 2 shows a transition between an expanding field of vectors and a compressing field of vectors. The border of the region within which the vectors describe an expansion, in particular an expansion in volume, is used to define the delineation. As shown in the embodiment of FIG. 2, the delineation 110 of the expanded structure 100 is defined such that it is equal to the border of the expansion region, in particular equal to the transition between the fields of expansion and compression. The transition is shown by the arrow 120 in FIG. 2. The transition 120 occurs between the delineation 110 of the expanded structure 100 and the delineation 210 of the compressed structure 200. As can be seen in FIG. 2, the length of the vectors are at a maximum at the delineation 110 of the expanded structure. In accordance with one embodiment, the delineation of the expanded structure is therefore defined on the basis of the positions at which the vector length is at a maximum.

Figure 3:
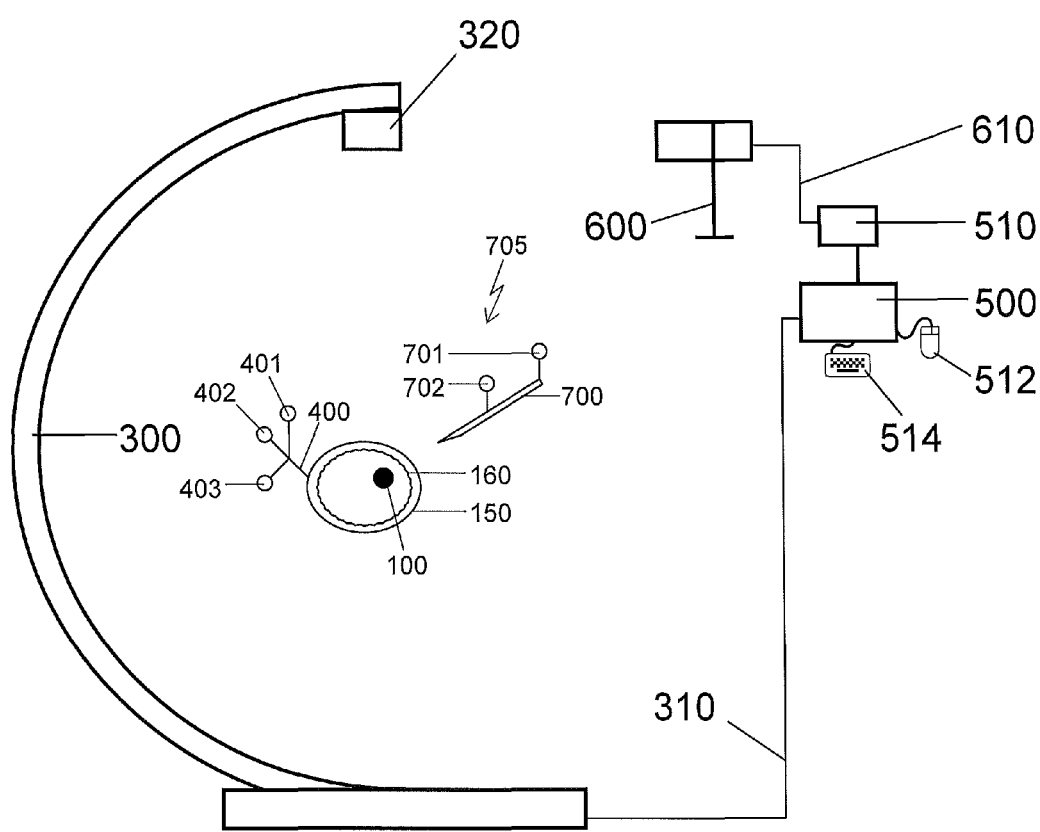
FIG. 3 shows a navigation system in accordance with an embodiment of the invention.

FIG. 3 shows a navigation system in accordance with an embodiment of the invention. A patient's body 150 comprises an anatomical structure 160, such as for example the brain. An physically-varying anatomical structure 100, for instance a tumour, is situated within the anatomical structure 160. The tumour 100 has compressed the healthy brain tissue around the tumour 100, hence there has been expansion within the region of the expanded structure 100 and compression within the region outside the structure 100. The above-mentioned first image, which does not show the physically-varying anatomical structure or only shows the physically-varying anatomical structure in a different physical state, has for example been generated before the growth of the tumour. In order to generate the first image, a so-called C-arc (also referred to as a C-arm) 300 is an example for the above-mentioned analytical devices (like MR devices, CT devices etc.) and is for example used to generate a two-dimensional and/or a three-dimensional image of the second anatomical part (for example, the brain). The C-arc is in particular constituted to generate three-dimensional images similar to those known from a CT. The same analytical device (i.e. for example the C-arc or MR device) 300 can subsequently be used to generate the second image which is a two-dimensional or three-dimensional image. The C-arc is schematically shown in FIG. 3 and bears the reference sign 300. The C-arc 300 for example comprises a fluoroscope 320 which is shown at the top of the arc in FIG. 3. The fluoroscope 320 preferably generates an image of both the second anatomical part (for example, the brain) and the marker device 400 which comprises the markers 401, 402 and 403. The marker device 400 is for instance attached to a bone structure such as for example the skull. The image data generated by the analytical device (i.e. for example the C-arc or the CT device) are transferred via a line 310 to the computer 500. The computer 500 preferably generates the three-dimensional image, in particular the first and/or second image. The second image preferably represents the marker device 400 and the second anatomical part including the physically-varying anatomical structure. The delineation of the physically-varying anatomical structure 100 is in particular not discernible in the second image. In order to determine the delineation of the physically-varying anatomical structure 100, the computer 500 preferably has a program loaded onto it which performs the data processing method described above. The program is in particular run on the computer 500. The program calculates the position of the delineation of the physically-varying anatomical structure 100 on the basis of the first and second images, as described further above. The relative position between the delineation of the physically-varying anatomical structure 100 and the marker device 400 is preferably determined, in particular calculated, by the computer 500. The computer 500 also receives data from a detection device 600 which is in particular a camera, in particular a stereoscopic camera. The detection device 600 transmits detection signals, received from the marker device 400, to the computer 500. The detection device 600 also receives detection signals from the instrument 700 which has two markers 701 and 702 attached to it which act as a marker device 705. The relative position between the marker device 705 (comprising the markers 701 and 702) and the instrument 700, in particular the tip of the instrument 700, is preferably stored in a database to which the computer 500 has access. The detection signals of the detection device 600, which represent the position of the marker devices 400 and 705, are thus preferably transmitted to the computer 500 via the line 610. The computer 500 preferably calculates the relative position between the marker device 705 and the marker device 400 on the basis of these detection signals. Since the relative position between the marker device 400 and the delineation of the physically-varying anatomical structure 100 has been calculated on the basis of the data processing method according to the present invention, the computer 500 can and preferably does then calculate the relative position between the marker device 705 and the delineation of the physically-varying anatomical structure 100. The computer 500 in particular determines the relative position between the tip of the instrument 700 (using the known relative position between the marker device 705 and the tip of the instrument 700) and the physically-varying anatomical structure 100, in particular the delineation of the physically-varying anatomical structure 100. The determined relative position between the instrument 700, in particular the tip of the instrument 700, and the physically-varying anatomical structure 100, in particular the delineation of the physically-varying anatomical structure 100, is shown on the display 510 of the computer 500. A mouse 512 and a keyboard 514 are attached to the computer 500 for inputting purposes.

The image displayed on the display 510 in particular shows the first and/or second anatomical part, in particular for example the brain or a part of it, and in particular the physically-varying anatomical structure 100 and a representation of the instrument 700, in particular in two or three dimensions.

The invention claimed is:

1. A data processing method for providing variation data that describe a non-enhancing tumor, comprising the steps of:
   providing second image data which describe a second image of a region of an anatomical body, wherein the region includes a second anatomical part which includes the non-enhancing tumor;
   providing first image data which represent a first image of the same region, wherein said same region includes a first anatomical part which does not include the non-enhancing tumor or which includes the non-enhancing tumor in a different physical state than in the second anatomical part;
   providing position change data which describe positional changes of corresponding image elements between the first image and the second image, on the basis of the first and second image data;
   and
   a) wherein the description of the positional changes provided by the position change data comprises change positions which define the positions at which the positional changes occur, and the method further comprises the steps of:
      determining the position at which the change in position is at a maximum;
      determining the variation data, which comprise a delineation of the non-enhancing tumor, on the basis of the positions at which the change is at a maximum, wherein the variation data further comprise a description of a position and geometry of the delineation of the non-enhancing tumor;
   or
   b) wherein:
      the positional changes are represented by a vector field; and
      determining the variation data comprises calculating a determinant of a Jacobian matrix of the vector field and of determining a position and geometry of a surface of the non-enhancing tumor by setting the determinant equal to 1.

2. The data processing method according to claim 1 wherein:
a) the first and second images describe the same region of the same anatomical body, wherein the first image was generated at an earlier point in time than the second image, wherein the non-enhancing tumor did not exist at said earlier point of time or was in a different physical state than at a later point in time at which the second image was generated; or
b) the first and second images describe the same region of a first and second anatomical body, respectively, wherein the first anatomical body is different to the second anatomical body and the first anatomical part of the first anatomical body does not include the non-enhancing tumor or only includes the non-enhancing tumor in a different physical state than in the second anatomical part; or
c) the first image data have been generated on the basis of third image data which describe a third image of another region which includes a third anatomical part, wherein the first and third anatomical parts are from the same anatomical body and the third anatomical part has a symmetry property such that a structure of the third anatomical part would be at least approximately symmetrical to the second anatomical part if the non-enhancing tumor had not grown in the region which includes the second anatomical part, wherein the first image data are generated from the third image data by transforming the third image data into the first image data in consideration of the symmetry property.

3. The data processing method according to claim 1, wherein the step of providing the position change data involves determining transformation data describing a transformation for one of the first and second images which, if applied to one of the first and second images, results in a transformed image which is at least similar to the other of the first and second images, and providing the position change data on the basis of the determined transformation data.

4. The data processing method according to claim 3 wherein the transformation data are determined using an image morphing algorithm.

5. The data processing method according to claim 1, further comprising the steps of:
providing correspondence data on the basis of the first and second image data, wherein the correspondence data comprise a description of correspondence pairs that are pairs of corresponding image elements of the first and second images, wherein a first element of the correspondence pair is an image element of the first image, and a second element of the correspondence pair is an image element of the second image, and wherein the first and second elements of the correspondence pair correspond to each other;
providing the position change data on the basis of the correspondence data;
wherein the position change data for at least some of the correspondence pairs describe a positional change in the corresponding image elements as a change from a position of one of the first and second elements of one of the correspondence pairs to a position of the other of the first and second elements of the same correspondence pair.

6. The data processing method according to claim 5, wherein the step of providing correspondence data comprises:
determining image indication data on the basis of the first and second image data, wherein the image indication data indicate the first and second image;
and receiving the correspondence data.

7. The data processing method accordingly to claim 5, wherein the step of providing correspondence data comprises:
providing image element data that describe a plurality of image elements;
determining two of the provided plurality of image elements to be corresponding image elements of a correspondence pair if the two image elements are described as corresponding to each other by received correspondence indication data.

8. The data processing method accordingly to claim 5, wherein the step of providing correspondence data comprises:
providing image element data that describe a plurality of image elements;
determining two of the provided plurality of image elements to be corresponding image elements of a correspondence pair if at least one of the following conditions applies:
image content of a first of the two image elements is at least similar to image content of a second of the two image elements; or
a first neighboring image element neighbors the first image element and forms a correspondence pair with a second neighboring image element which neighbors the second image element, wherein a relative position between the first neighboring image element and the first image element is at least similar to a relative position between the second neighboring image element and the second image element, and this similarity in the relative positions is given for a plurality of first and second neighboring image elements; or
if the two of the provided plurality of image elements are transformed into each other by a transformation which transforms one of the first and second images into the other of the first and second images.

9. The data processing method according to claim 1, wherein the first and second images are registered with respect to each other on the basis of corresponding image elements which have not changed their position, and the position change data are provided on the basis of the registered images.

10. The data processing method according to claim 1, wherein the method further comprises the steps of:
determining compression-variation data that describe where a transition between a compression and an expansion occurs, on the basis of the positional changes and the change positions; and
determining the variation data by determining a delineation of the non-enhancing tumor on the basis of the compression-variation data.

11. The data processing method according to claim 1, wherein the step of providing the variation data comprises the steps of:
determining change indication data on the basis of the position change data, wherein the change indication data indicate at least one of the following:
changes in volume between the first and second images; or positional changes between the first and second images; and receiving the variation data.

12. A method for navigating an instrument, comprising the steps of:
performing the steps of the method of claim 1 in order to determine the variation data;
providing instrument position data which describe a position of an instrument;
providing body part position data which describe the position of the second anatomical part; and
determining the relative position of the instrument relative to the non-enhancing tumor on the basis of the variation data, the instrument position data and the body part position data, in order to navigate the instrument.

13. A non-transitory computer readable storage medium storing a program which, when running on a computer or when loaded onto a computer, causes the computer to perform a method for providing variation data that describe a non-enhancing tumor, comprising:
providing second image data which describe a second image of a region of an anatomical body, wherein the region includes a second anatomical part which includes the non-enhancing tumor;
providing first image data which represent a first image of the same region, wherein said same region includes a first anatomical part which does not include the non-enhancing tumor or which includes the non-enhancing tumor in a different physical state than in the second anatomical part;
providing position change data which describe positional changes of corresponding image elements between the first image and the second image, on the basis of the first and second image data; and
a) wherein the description of the positional changes provided by the position change data comprises change positions that define the positions at which the positional changes occur, and the method further comprises the steps of:
determining the position at which the change in position is at a maximum;
determining the variation data, which comprise a delineation of the non-enhancing tumor, on the basis of the positions at which the change is at a maximum, wherein the variation data further comprise a description of a position and geometry of the delineation of the non-enhancing tumor; or
b) wherein:
the positional changes are represented by a vector field; and
determining the variation data comprises calculating a determinant of a Jacobian matrix of the vector field and of determining a position and geometry of a surface of the non-enhancing tumor by setting the determinant equal to 1.

14. The data processing method according to claim 1, further comprising at least one of:
performing, by an analytical device operably associated with a computer, an analysis of a body for generating the second image data;
detecting by a detection device operably associated with the computer, a position of an instrument;
detecting by the detection device a position of a second anatomical part; or
outputting, via an interface operably associated with the computer, an indication signal, in order to indicate at least one of the following:
the position change data;
the magnitude of positional changes of correspondence pairs;
the direction of positional changes of correspondence pairs;
the position of the non-enhancing tumor;
the geometry of the non-enhancing tumor;
a position of a delineation of the non-enhancing tumor;
a geometry of the delineation of the non-enhancing tumor; or
the relative position between the instrument and the non-enhancing tumor;
wherein the interface converts data outputted by the computer into the indication signal.

* * * * *